United States Patent
Banik

(10) Patent No.: US 7,128,707 B2
(45) Date of Patent: *Oct. 31, 2006

(54) ELECTROACTIVE POLYMER BASED ARTIFICIAL SPHINCTERS AND ARTIFICIAL MUSCLE PATCHES

(75) Inventor: Michael S. Banik, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/188,368

(22) Filed: Jul. 25, 2005

(65) Prior Publication Data

US 2005/0256367 A1  Nov. 17, 2005

Related U.S. Application Data

(63) Continuation of application No. 10/825,860, filed on Apr. 16, 2004, now Pat. No. 6,921,360, which is a continuation of application No. 10/142,861, filed on May 10, 2002, now Pat. No. 6,749,556.

(51) Int. Cl.
*A61F 2/00* (2006.01)

(52) U.S. Cl. .......................... 600/30; 600/16

(58) Field of Classification Search ............ 600/29–32, 600/16–18, 37; 128/DIG. 25
See application file for complete search history.

(56) References Cited

U.S. PATENT DOCUMENTS

| | | | | |
|---|---|---|---|---|
| 4,222,377 A | 9/1980 | Burton | ......................... | 128/1 R |
| 4,571,749 A | 2/1986 | Fischell | ......................... | 623/14 |
| 4,587,954 A | 5/1986 | Haber | ......................... | 128/1 R |
| 4,878,889 A | 11/1989 | Polyak | ......................... | 600/31 |
| 5,100,933 A | 3/1992 | Tanaka et al. | ............. | 523/300 |
| 5,250,167 A | 10/1993 | Adolf et al. | ................ | 204/209 |
| 5,389,222 A | 2/1995 | Shahinpoor | ................ | 204/299 |
| 5,556,700 A | 9/1996 | Kaneto et al. | ............... | 428/332 |
| 5,562,598 A | 10/1996 | Whalen et al. | ................ | 600/29 |
| 5,603,337 A | 2/1997 | Jarvik | ......................... | 128/898 |
| 5,631,040 A | 5/1997 | Takuchi et al. | ............. | 427/100 |
| 5,702,343 A | 12/1997 | Aferness | ...................... | 600/37 |
| 5,738,626 A | 4/1998 | Jarvik | ......................... | 600/16 |
| 5,800,528 A | 9/1998 | Lederman et al. | ............. | 623/3 |
| 5,855,565 A | 1/1999 | Bar-Cohen et al. | ......... | 604/104 |
| 5,888,188 A | 3/1999 | Srougi et al. | ................. | 600/30 |
| 5,893,826 A | 4/1999 | Salama | ........................ | 600/31 |

(Continued)

FOREIGN PATENT DOCUMENTS

WO  WO 97/26039  7/1997

(Continued)

OTHER PUBLICATIONS

Brock, David L. "Review of Artificial Muscle Based on Contractile Polymers". Massachusetts Institute of Technology Artificial Intelligence Laboratory. A.I. Memo No. 1330, Nov. 1991. 11. 1-12.

(Continued)

*Primary Examiner*—John P. Lacyk
(74) *Attorney, Agent, or Firm*—Mayer & Willams PC; David B. Bonham, Esq.

(57) ABSTRACT

Provided are artificial muscle patches, which are adapted to be implanted adjacent a patient's heart, and artificial sphincter cuffs, which are adapted to be implanted around a body lumen, such as the urethra, the anal canal, or the lower esophagus. The devices of the present invention comprise: (a) one or more electroactive polymer actuators; and (b) a control unit for electrically controlling the one or more electroactive polymer actuators to expand or contract the devices.

44 Claims, 13 Drawing Sheets

U.S. PATENT DOCUMENTS

| | | | |
|---|---|---|---|
| 6,022,312 A | 2/2000 | Chaussy et al. | 600/29 |
| 6,095,968 A | 8/2000 | Snyders | 600/16 |
| 6,109,852 A | 8/2000 | Shahinpoor et al. | 414/1 |
| 6,162,238 A | 12/2000 | Kaplan et al. | 606/201 |
| 6,190,408 B1 | 2/2001 | Melvin | 623/3.1 |
| 6,249,076 B1 | 6/2001 | Madden et al. | 310/363 |
| 6,293,906 B1 | 9/2001 | Vanden Hoek et al. | 600/37 |
| 6,302,917 B1 | 10/2001 | Dua et al. | 623/23.68 |
| 6,514,237 B1 | 2/2003 | Maseda | 604/533 |
| 6,749,556 B1 | 6/2004 | Banik | 600/30 |
| 6,921,360 B1 * | 7/2005 | Banik | 600/30 |

FOREIGN PATENT DOCUMENTS

| | | |
|---|---|---|
| WO | WO 01/58973 | 8/2001 |

OTHER PUBLICATIONS

"Important Information for Patients Considering an Action Neosphincter", http://www.fda.gov/ohrms/dockets/ac/01/briefing/3777b1_02_patient_info.pdf.

Bar-Cohen, Yoseph, Ed. Electroactive Polymer (EAP) Actuators as Artifical Muscles: Reality, Potential and Challenges, SPIE Press, 2001, Chapter 1, pp. 3-44.

Bar-Cohen, Yoseph, Ed. Electroactive Polymer (EAP) Actuators as Artifical Muscles: Reality, Potential and Challenges, SPIE Press, 2001, Chapter 7, pp. 193-221.

Bar-Cohen, Yoseph, Ed. Electroactive Polymer (EAP) Actuators as Artifical Muscles: Reality, Potential and Challenges, SPIE Press, 2001, Chapter 16, pp. 457-495.

Bar-Cohen, Yoseph, Ed. Electroactive Polymer (EAP) Actuators as Artifical Muscles: Reality, Potential and Challenges, SPIE Press, 2001, Chapter 21, pp. 615-659.

Bar-Cohen, Yoseph, Ed. WorldWide ElectroActive Polymers (Artificial Muscles) Newsletter, vol. 3. No. 1. Jun. 2001. pp. 1-14.

Shahinpoor, Moshen et al. "Design, Development and Testing of a Multi-Fingered Heart Commpression/ Assist Device Equipped with IPMC Artificial Muscles". Smart Structures and Materials 2001: Electroactive Polymer Actuators and Devices. Yoseph Bar-Cohen, SPIE Proces. vol. 4329. 2001. pp. 411-420.

Jager, Edwin W.H. et al."Microfabricating Conjugated polymer actuators". Smart Structures and Materials 2001: Electroactive Polymer Actuators and Devices, Proceedings of the SPIE. vol. 4329. pp. 335-349.

Pelrine, Ron et al. "Applications of Dielectric Elastomer Acuators". Smart Structures and Materials 2001: Electroactive Polymer Actuators and Devices, Proceedings of the SPIE. vol. 4329. pp. 335-349.

Madden, John D.W. "Polypyrrole actuators: modeling a performance". Smart Structues and Materials: Electroactive Polymer Actuators and Devices, Proceedings of the SPIE. vol. 4329. pp. 72-83, 2001.

Bar-Cohen, Yoseph. "Transition of EAP material from novelty to proactical application-are we there yet". Smart Strucutures and Material. 2001. Electroactive Polymer Actuators and Devices proceedings of the APIE. col. 4329. pp. 1-6.

* cited by examiner

ELECTROACTIVE POLYMER BASED ARTIFICIAL SPHINCTERS AND ARTIFICIAL MUSCLE PATCHES

STATEMENT OF RELATED APPLICATION

This application is a continuation of U.S. patent application Ser. No. 10/825,860, filed Apr. 16, 2004 now U.S. Pat. No. 6,921,360, entitled "Electroactive Polymer Based Artificial Sphincters and Artificial Muscle Patches," which is a continuation of U.S. patent application Ser. No. 10/142,861, filed May 10, 2002, now U.S. Pat. No. 6,749,556, both of which are incorporated by reference in their entireties herein.

FIELD OF THE INVENTION

The present invention relates to medical devices, and more particularly to artificial sphincters and artificial muscle patches that are based on electroactive polymers.

BACKGROUND OF THE INVENTION

Millions of Americans are incontinent. Incontinence is the second most common reason for institutionalization of the elderly, generating costs of several billion dollars per year. Incontinence commonly arises from malfunction of the urethral sphincter. The urethral sphincter is an external sphincter formed about the urethra in both males and females which, when functioning normally, constricts the urethra and prevents flow of urine from the bladder, except when the bladder is voided during normal urination. Unfortunately, a spectrum of medical conditions can result in improper functioning of the urethral sphincter and lead to incontinence, including surgical injury following transurethral resection or radical prostatectomy, neurologic injury, or direct injury to the sphincter itself.

There are numerous prior art prosthetic sphincters for selectively closing and opening the urethra to prevent incontinence. These devices typically incorporate an inflatable cuff which surrounds the urethra, and which is inflated to restrict urine flow in the urethra. Examples of such prosthetic sphincters are seen in U.S. Pat. Nos. 4,222,377, and 5,562,598. These patents describe devices having an inflatable urethral cuff, a balloon reservoir/pressure source, and a pump. The cuff is typically implanted around the bladder neck in women, and around the bulbous urethra in most men. The implanted cuff functions similarly to a blood pressure cuff.

Fecal incontinence, like urinary incontinence is a debilitating condition affecting tens of thousands of Americans. Fecal incontinence in both men and women is typically caused by neurological or muscular dysfunction of the anal sphincter, and is commonly the result of trauma.

As with urinary incontinence, prosthetic sphincters for selectively closing and opening the anal canal to prevent fecal incontinence have been developed. One such sphincter, which is approved for use by the FDA, is available from American Medical Systems under the name Acticon™ Neosphincter. As with the above artificial sphincters for urinary incontinence, these devices incorporate an inflatable cuff that functions similar to a blood pressure cuff and is inflated to restrict fecal flow. These devices also include a balloon reservoir/pressure source and a pump.

The above artificial urethral and anal sphincters, however, are cumbersome and limited, and complications occur in a high percentage of patents. Moreover, because the system is a pressurized system, it is vulnerable to leakage of the pressurized fluid.

These and other drawbacks of prior art artificial urethral and anal sphincters are addressed by a first aspect of the present invention, in which an artificial sphincter is provided that is based on electroactive polymers under electronic control.

Gastro-esophageal reflux disease (GERD) is a condition characterized by the reflux of stomach contents, including stomach acid, into the esophagus. Approximately 5 million people in the United States alone experience chronic GERD. Of these, approximately 60–65% suffer from lower esophageal sphincter dysfunction, which is typically characterized by a weakening of the lower esophageal sphincter.

The lower esophageal sphincter is a ring of smooth muscle at the bottom few centimeters of the esophagus. In its resting state, the lower esophageal sphincter creates a region of high pressure at the orifice to the stomach. This pressure is critical to the proper operation of the lower esophageal sphincter.

The lower esophageal sphincter opens in response to the peristaltic motion that is triggered when food or beverage enters the esophagus. After food passes into the stomach, the peristaltic motion ceases, and the lower esophageal sphincter returns to its normal resting state to prevent reflux of the stomach contents, including stomach acid, back into the esophagus.

Current treatment options for GERD include various endoscopic, laproscopic and pharmaceutically-based therapies, such as fundoplication, RF ballooning, and powerful acid suppressing pharmaceuticals such as Zantac® (ranitidine), Tagamet® (cimetidine) and Pepcid® (famotidine). While these options offer a highly focused therapeutic potential, they fail in providing a long-term cure, and are not conducive to patient comfort.

As such, the need for a more dynamic and versatile option for the long-term treatment of GERD is apparent. To that end, in another aspect of the present invention, an artificial lower esophageal sphincter is provided, which is based on electroactive polymers that are under electronic control.

Congestive heart failure is a progressive and debilitating illness. The disease is characterized by a progressive enlargement of the heart. As the heart enlarges, it is required to perform an increasing amount of work in order to pump blood with each heartbeat. In time, the heart becomes so enlarged that it cannot adequately supply blood. An afflicted patient is fatigued, unable to perform even simple exerting tasks, and experiences pain and discomfort.

Millions of Americans suffer from congestive heart failure, with economic costs of the disease having been estimated at tens of billions of dollars annually.

Patients suffering from congestive heart failure are commonly grouped into four classes (i.e., Classes I, II, III and IV). In the early stages (e.g., Classes I and II), drug therapy is the most commonly prescribed treatment. Drug therapy treats the symptoms of the disease and may slow the progression of the disease. Unfortunately, there is presently no cure for congestive heart failure. Even with drug therapy, the disease will progress. Further, the drugs may have adverse side effects.

One treatment for late-stage congestive heart failure is heart transplant.

However, even if the patient qualifies for transplant and a heart is available for transplant, it is noted that heart transplant procedures are very risky, invasive, expensive and only shortly extend a patient's life. For example, prior to transplant, a Class IV patient may have a life expectancy of 6 months to one-year. Heart transplant may improve the expectancy to about five years. Similar risks and difficulties exist for mechanical heart transplants as well.

Another technique for the treatment for late stage congestive heart failure is a cardiomyoplasty procedure. In this procedure, the latissimus dorsi muscle (taken from the patient's shoulder) is wrapped around the heart and electrically paced synchronously with ventricular systole. Pacing of the muscle results in muscle contraction to assist the contraction of the heart during systole. However, even though cardiomyoplasty has demonstrated symptomatic improvement, studies suggest the procedure only minimally improves cardiac performance. Moreover, the procedure is highly invasive, expensive and complex, requiring harvesting a patient's muscle and an open chest approach (i.e., sternotomy) to access the heart.

Recently, a new surgical procedure, referred to as the Batista procedure, has been developed. The procedure includes dissecting and removing portions of the heart in order to reduce heart volume. However, the benefits of this surgery are controversial, the procedure is highly invasive, risky and expensive, and the procedure commonly includes other expensive procedures (such as a concurrent heart valve replacement). Also, if the procedure fails, emergency heart transplant is essentially the only available option.

Others have used external constraints such as jackets, girdles, fabric slings or clamps to constrain and remodel the heart and reduce heart volume. See, e.g., U.S. Pat. No. 6,293,906 (citing numerous references including U.S. Pat. No. 5,702,343 and U.S. Pat. No. 5,800,528) and U.S. Pat. No. 6,095,968. In accordance with an example from the above '906 patent, a cardiac constraint device can be placed on an enlarged heart and fitted snug during diastole; for example, a knit jacket device can be loosely slipped on the heart, the material of the jacket can be gathered to adjust the device to a desired tension, and the gathered material can be sutured or otherwise fixed to maintain the tensioning.

As an improvement upon the above and in accordance with a further aspect of the present invention, an artificial muscle patch is provided, which is based on electroactive polymers that are under electronic control. The artificial muscle patch provides cardiac constraint and, if desired, can be electrically paced (e.g., synchronously with ventricular systole) to improve cardiac performance.

SUMMARY OF THE INVENTION

According to a first aspect of the invention, an artificial sphincter is provided, which comprises: (a) a cuff that is adapted for placement around a body lumen, which cuff comprises one or more electroactive polymer actuators; and (b) a control unit for electrically controlling the one or more electroactive polymer actuators to expand or contract the cuff.

The one or more electroactive polymer actuators of the artificial sphincter can beneficially comprise (a) one or more active members, (b) a counter-electrode, and (c) an electrolyte disposed between the active member and the counter-electrode.

In some preferred embodiments, the active members are disposed upon one or more substrate layers. The active members can be provided in numerous configurations on the substrate layer(s), including nonlinear configurations that are capable of exerting force vectors along at last two axes, for instance, an S-shaped configuration. The substrate layer(s) can be insulating or conductive in nature. Where insulating, it may be preferred to provide conductive lines on the substrate layer(s) to allow electrical communication between active members and the power source.

In certain embodiments, the cuff will further comprise a barrier layer and/or a mesh layer.

The action of the artificial sphincter of the present invention can be controlled using a variety of control units, for example, (a) power source and a simple switch or (b) power source and a logic/control device such as a computer.

In some embodiments, the cuff is provided with a restoring force to bring it into an expanded or a contracted state, preferably by including at least one elastic structural element within the cuff to supply such a restoring force. For example, the artificial sphincter cuff can be provided with an elastic annular tube structure whose length increases upon a decrease in its cross-sectional diameter.

The artificial sphincters of the present invention can also comprise a sensing system (such as a system comprising strain gauges) for sensing the degree of contraction of the electroactive polymer actuators.

Opposing ends of the artificial sphincter cuffs of the present invention may be provided with fasteners for securing the cuff around the body lumen.

The artificial sphincter cuffs of the present invention may be adapted for placement around a number of body lumens, including the urethra, the anal canal, and the lower esophagus.

A lower esophageal sphincter in accordance with the present invention can be provided, for example, with sensing system that detects when food or beverage enters the esophagus, or with a sensing system that detects when the stomach is attempting to regurgitate its contents.

Other embodiments are directed to the treatment of fecal incontinence, urinary incontinence or gastro-esophageal reflux disease by implanting into a patient an artificial sphincter in accordance with the present invention.

One advantage of this aspect of the present invention is that artificial sphincters are provided, which address fecal or urinary incontinence in a patient.

This aspect of the present invention is also advantageous in that an apparatus is provided, which offers a relatively instantaneous way to empty the bladder/lower bowel.

This aspect of the present invention is further advantageous in that artificial urethral and anal sphincters are provided, which are based on electroactive polymers under electronic control. As a result, a pressurized system such as that used in the prior art, with concomitant vulnerability to leakage of the pressurized fluid, is avoided.

Another advantage of this aspect of the present invention is that an artificial lower esophageal sphincter is provided, which compensates for lower esophageal sphincter dysfunction in a patient.

Another advantage this aspect of the present invention is that a long-term cure for GERD is provided.

A further advantage of this aspect of the present invention is that an artificial lower esophageal sphincter is provided, which is based on electroactive polymers under electronic control.

According to another aspect of the present invention, an artificial muscle patch is provided, which is adapted to be implanted adjacent a patient's heart. The artificial muscle patch comprises: (a) one or more electroactive polymer actuators; and (b) a control unit for electrically controlling the one or more electroactive polymer actuators to expand or contract the artificial muscle patch.

As above, the one or more electroactive polymer actuators of the artificial muscle patch can beneficially comprise (a) one or more active members, (b) a counter-electrode, and (c) an electrolyte disposed between the active member and the counter-electrode. In some preferred embodiments, the active members are disposed upon one or more substrate layers. The active members can be provided in numerous configurations on the substrate layer(s), including nonlinear configurations that are capable of exerting force vectors along at last two axes, for example, an S-shaped configuration. The substrate layer(s) can be insulating or conductive in nature. Where insulating, it may be preferred to provide conductive lines on the substrate layer(s) to allow electrical communication between active members and the power source. In certain embodiments, the patch will also further comprise a barrier layer and/or a mesh layer.

The action of the artificial muscle patch of the present invention can be controlled using a variety of control units, for example, (a) a power source and a simple switch or (b) power source and a logic/control device such as a computer.

The artificial muscle patch can further comprise a sensing system for detecting a patient's heartbeat, in which case the control unit preferably paces the contraction and expansion of the electroactive polymer actuators with the heartbeat.

Alternatively, the control unit can pace both the heart as well as the contraction and expansion of said electroactive polymer actuators.

Other embodiments are directed to the treatment of congestive heart failure by implanting into a patient an artificial muscle patch in accordance with the present invention.

One advantage of this aspect of the present invention is that an artificial muscle patch is provided, which is based on electroactive polymers under electronic control.

Another advantage of this aspect of the present invention is that a device is provided, which can supply cardiac constraint and, if desired, can be electrically paced to improve cardiac performance.

A further advantage of this aspect of the present invention is that a device is provided, which can supply cardiac constraint via a procedure that is considerably less invasive and more simplified that many prior art techniques for surgically addressing congestive heart failure.

These and other embodiments and advantages will become immediately apparent to those of ordinary skill in the art upon review of the Detailed Description and Claims to follow.

DETAILED DESCRIPTION OF THE INVENTION

The present invention relates to medical devices, such as artificial sphincters and artificial muscle patches, which are operated using electroactive-polymer-based actuators.

Electroactive polymers, also referred to as "conductive polymers" or "conducting polymers," are characterized by their ability to change shape in response to electrical stimulation. They typically structurally feature a conjugated backbone and have the ability to increase electrical conductivity under oxidation or reduction. Some common electroactive polymers are polyaniline, polypyrrole and polyacetylene. Polypyrrole is pictured below:

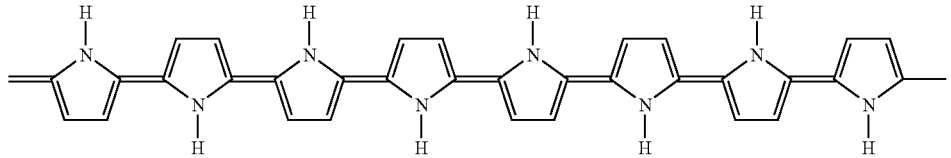

These materials are typically semi-conductors in their pure form. However, upon oxidation or reduction of the polymer, conductivity is increased. The oxidation or reduction leads to a charge imbalance that, in turn, results in a flow of ions into or out of the material in order to balance charge. These ions, or dopants, enter the polymer from an ionically conductive electrolyte medium that is coupled to the polymer surface. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, the expansion is due to ion insertion between chains, whereas in others interchain repulsion is the dominant effect. Thus, the mass transfer of ions both into and out of the material leads to expansion or contraction of the polymer.

Currently, linear and volumetric dimensional changes on the order of 25% are possible. The stress arising from the dimensional change can be on the order of 3 MPa, far exceeding that exerted by smooth muscle cells.

Figure 1:
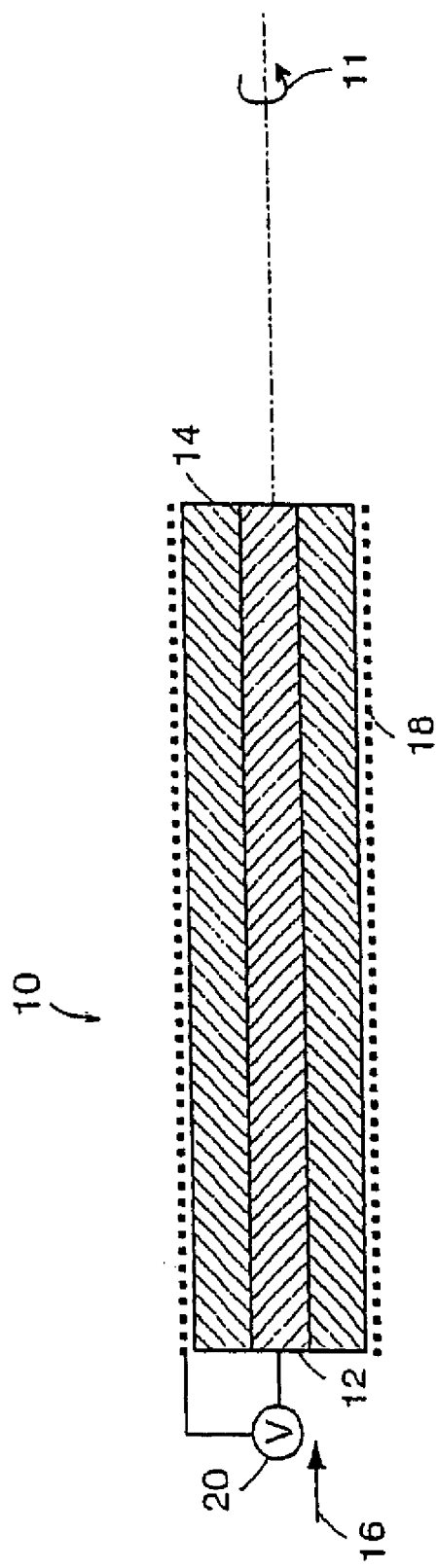
FIG. 1 is a schematic diagram of an actuator useful in the present invention.

Referring now to FIG. 1, an actuator 10 is shown schematically in cross-section. Active member 12 of actuator 10 has a surface coupled with electrolyte 14 and has an axis 11. Active member 12 includes a conducting polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in concert for applying a tensile force in a longitudinal direction substantially along axis 11. The fibers may be bundled or distributed within the electrolyte 14.

Active member 12 includes an electroactive polymer. Many electroactive polymers having desirable tensile properties are known to persons skilled in the art. In accordance with preferred embodiments of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," Synthetic Metals, vol. 36, pp. 209–224 (1988), which is incorporated herein by reference. In addition to polypyrrole, any conducting polymer that exhibits contractile properties may be used within the scope of the invention. Polyaniline is another example of such a usable conducting polymer.

From an energy standpoint, it may be preferable to configure the devices of the present invention such that the electroactive polymers constrict where no potential is applied (i.e., under steady state conditions) and expand upon the application of an appropriate voltage, or vice versa. For example, the electrolyte composition can frequently be modified to achieve the desired steady-state configuration (e.g., by selecting appropriate ionic species and/or ionic species concentration). However, other actuators types are clearly appropriate.

Electrolyte 14 may be a liquid, a gel, or a solid, so long as ion movement is allowed. Moreover, where the electrolyte 14 is a solid, it should move with the active member 12 and should not be subject to delamination. Where the electrolyte 14 is a gel, it may be, for example, an agar or polymethylmethacrylate (PMMA) gel containing a salt dopant. Where the electrolyte is a liquid, it may be, for example, a phosphate buffer solution, potassium chloride, sodium chloride, or fluorinated organic acids. The electrolyte is preferably non-toxic in the event that a leak occurs in vivo.

Counter-electrode 18 is in electrical contact with electrolyte 14 in order to provide a return path for charge to a source 20 of potential difference between member 12 and electrolyte 14. Counter-electrode 18 may be any electrical conductor, for example, another conducting polymer, a conducting polymer gel, or a metal such as gold. In order to activate actuator 10, a current is passed between active member 12 and counter-electrode 18, inducing contraction or expansion of member 12. Additionally, the actuator preferably has a flexible barrier layer for separating the electrolyte from an ambient environment.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72–83), both of which are hereby incorporated by reference in their entirety.

Figure 2A:
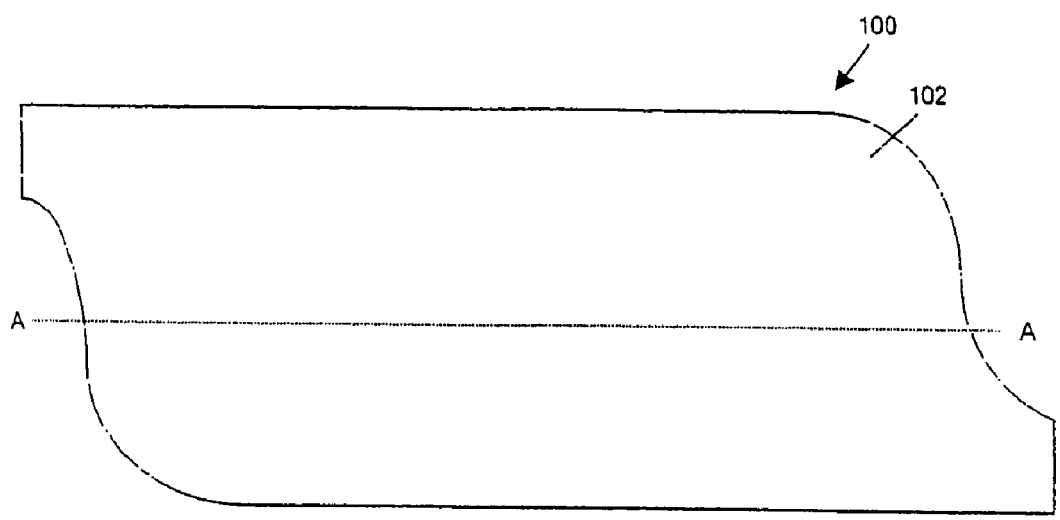
FIG. 2A is a schematic plan view of an artificial sphincter cuff in accordance with an embodiment of the invention.

Referring to FIG. 2A, an artificial sphincter cuff 100 is illustrated in accordance with one embodiment of the present invention. The artificial sphincter cuff 100 is adapted to be wrapper around a body lumen of interest, whereupon opposing ends of the artificial sphincter cuff are secured to one another. For example, in the embodiment of the invention illustrated in FIG. 2A, the artificial sphincter cuff is equipped with holes 102 (one numbered), which allow the device to be laced in place after wrapping around a lumen of interest, for example, using suture materials.

Figure 4:
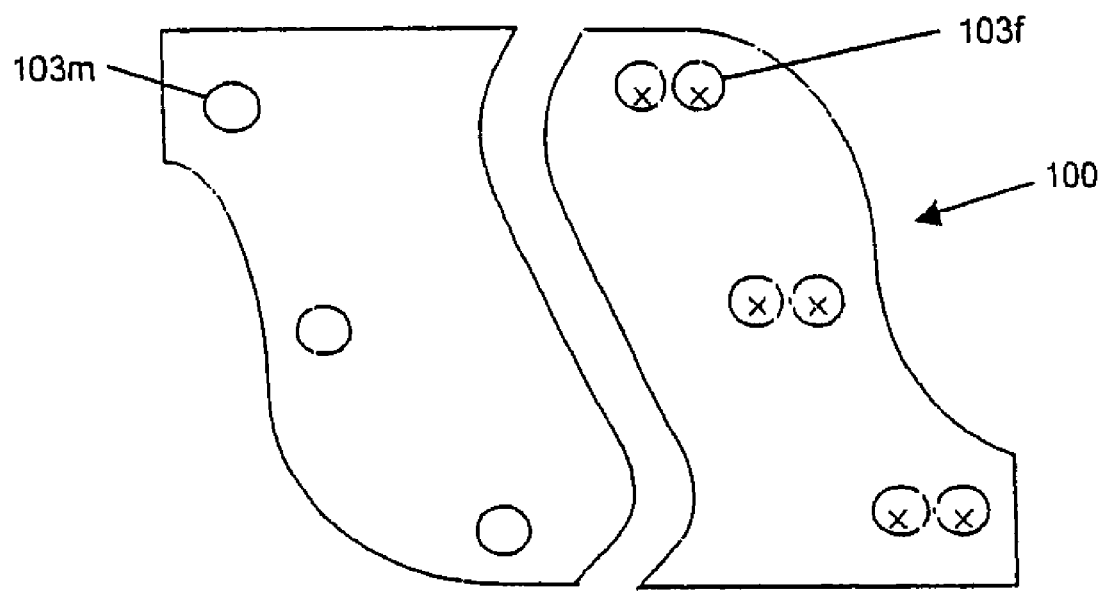
FIG. 4 is a schematic partial plan view of an artificial sphincter cuff in accordance with another embodiment of the invention, which illustrates snap portions useful for securing opposite ends of the sphincter cuff to one another.

Of course, numerous other embodiments for securing the opposing ends of the artificial sphincter cuff 100, other than the embodiment of FIG. 2A, are possible. For example, as illustrated in FIG. 4, snaps can be used. Male snap portions 103m (one numbered) are provided on one end, while female snap portions 103f (one numbered) are provided on the opposite end. By using a series of snaps on one end (for example, two rows of female snap portions 103f are provided in FIG. 4), the tension of the artificial sphincter in its initial position can be adjusted. Still other alternate embodiments are possible, including other securing systems having male-female components (e.g., plastic ratchet mechanisms like those commonly used in connection with electronic wire tie wrappers). Alternatively, the device can be provided with suture holes at various points along its length for suturing the device into place.

The actuators can be disposed within the artificial sphincter cuffs of the present invention in a number of ways. For example, the actuators can be separately manufactured and subsequently attached to the artificial sphincter. Alternatively, the actuators can be integrated into the device, for example by disposing arrays of active members upon one or more sheets of substrate material.

Figure 2B:
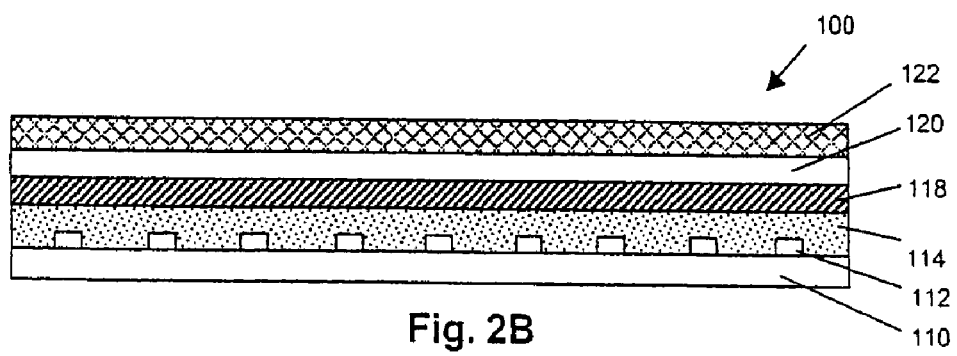
FIG. 2B is a schematic cross-sectional view of the artificial sphincter cuff of FIG. 2A, taken along ling A–A'.

One specific configuration is illustrated in FIG. 2B, which is a cross-section taken along line A–A' of the device of FIG. 2A. FIG. 2B illustrates a substrate layer 110 upon which several active members 112 (one numbered) are disposed, for example, by a transfer printing or deposition processes (including electrodeposition or vacuum deposition techniques). An electrolyte-containing layer 114 is disposed over the active member(s) 112, and a counter-electrode 118 is in turn disposed over the electrolyte-containing layer 114. Barrier layer 120 and mesh layer 122 are provided over counter-electrode 118. In this way, the device 100 is configured in the form of a thin-film, tape-like structure, enabling a low profile delivery around the body lumen of interest.

Figure 3A:
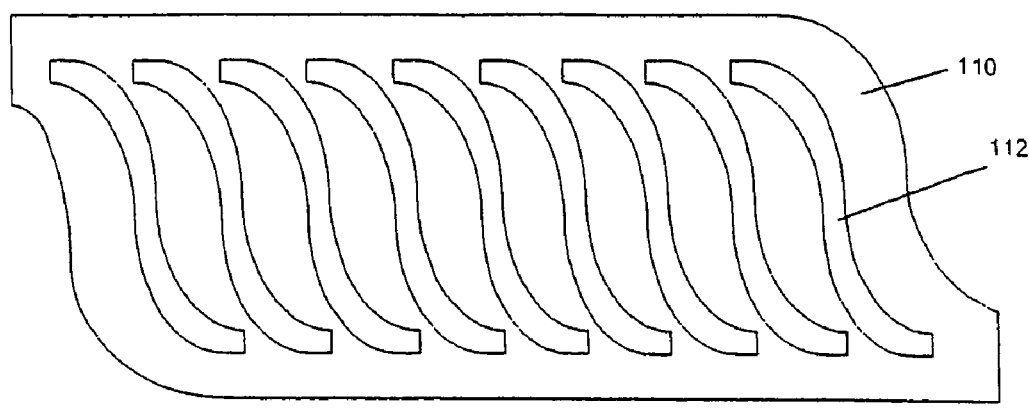
FIGS. 3A–3D are schematic plan views illustrating active members disposed on a substrate layer in various possible layouts, in accordance with several embodiments of the invention.

A plan view of the substrate layer 110 with active members 112 of FIG. 2B is illustrated in FIG. 3A. In this figure, nine active members 112 (one numbered) are shown disposed on the substrate layer 110. The nonlinear, s-shaped configuration of the active members 112 allows for a contraction force having force vectors along two axes, for example, horizontal and vertical vectors.

Figure 3B:
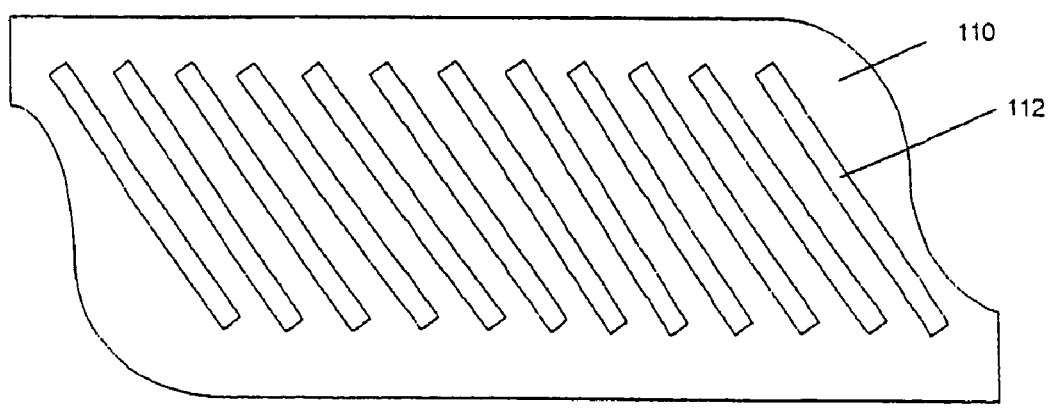
Figure 3C:
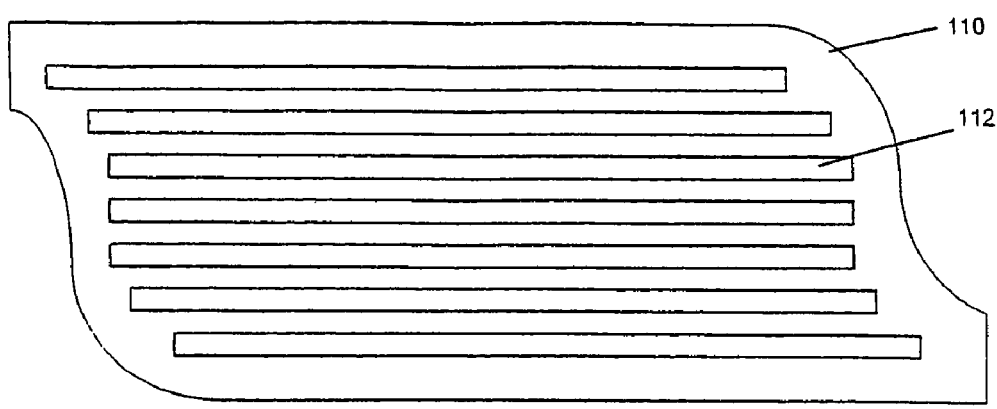

Of course, the active members 112 can be disposed on the substrate layer 110 in any number of configurations. For example, FIG. 3B illustrates a substrate 110 that has twelve diagonal active members 112 (one numbered) disposed upon it. This configuration results contraction forces having both vertical and horizontal vector components. FIG. 3C, on the other hand, illustrates seven active members 112 (one numbered) disposed on a substrate 110. In contrast to the configurations of FIGS. 3A and 3B, however, the configuration illustrated in FIG. 3C results in contraction forces having a predominantly horizontal component.

Figure 3D:
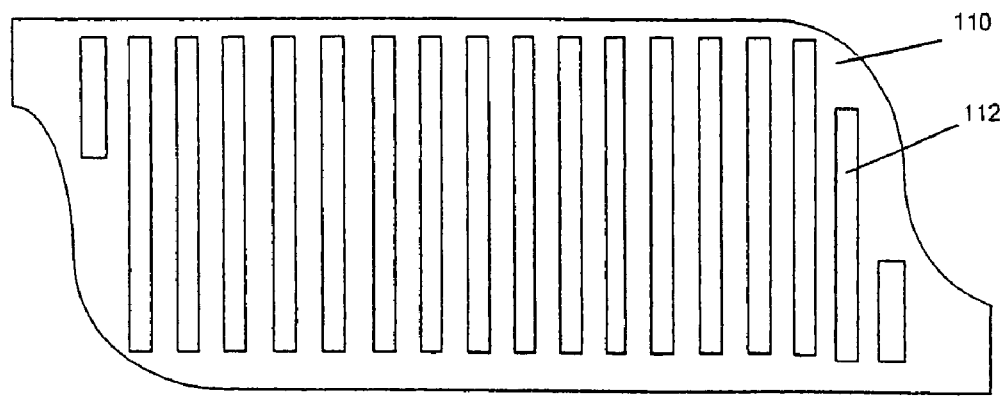

Multiple layers of actively members 112 are also possible. For example, it is possible to combine a substrate layer 110 having horizontal active members 112 like that illustrated in FIG. 3C with a substrate layer 110 having vertical active members 112 like that illustrated in FIG. 3D, to provide a contraction force having both horizontal and vertical vectors.

As discussed above, beneficial materials for use in the construction of the active members 112 include electroactive polymer materials known in the art such as polyaniline, polypyrrole, and polyacetylene.

To allow operation of the active members 112, the active members 112 and the counter-electrode 118 are typically connected to the appropriate terminals of a voltage source using any appropriate electrical connector. In other embodiments, however, it may be desirable to connect only one of (a) the active members 112 or (b) the counter-electrode to the power source, while grounding the other of (a) and (b), using the body as a ground, for example.

Where the active members are controlled as a group, a simple switch can be used as a control unit to activate them. Where individual control is desired, on the other hand, each active member is preferably in communication with, and is individually controllable by, a computer or other suitable control unit. This allows the control unit to individually perform operations on each active member for the purpose of effecting changes to the configuration of the overall device, for example, as a function of time.

The active members may be in direct communication with the control unit by means of individual dedicated circuits linking each of these elements to the control unit. Alternatively, it is also possible to place each active member is in communication with the control unit using a common communications cable. The signals to each active member are typically analog. If need be, digital-to-analog or analog-to-digital converters may be provided to convert the signals from one format to the other. The signals to each active member may be conveniently managed and transmitted over a common cable by multiplexing. Multiplexing schemes that may be used for this purpose include frequency-division multiplexing, wave-division multiplexing, or time-division multiplexing. Suitable multiplexers and demultiplexers can be employed at each end of the cable and along its length at the position of each actuator.

Numerous types of electrical connectors are possible. For example, distinct electrical cables can be connected to the active member of each actuator. Alternatively, the electrical connections can be printed onto a sheet. As one example, electrically conductive lines (e.g., lines of conductive polymer, doped polymer, or metal) can be printed onto a sheet containing the active elements, such as an insulating substrate layer 110. Such a sheet is analogous to a flexible printed circuit board in that the necessary elements are printed upon a flexible substrate. For example, the printed lines can include a central cable with individual track wires extending from the central cable to each active member 112. As discussed above, if individual activation of the actuators is desired, the cable can be activated, for example, using an appropriate multiplexing scheme. On the other hand, if the active members are to be activated simultaneously, the central cable can then simply be activated, for example, by a switch.

Electrical interconnect wiring can also be provided on a layer that is separate from the layer containing the active members 112, for example, using plated through-holes or vias (these can also function as "rivets" to hold the composite together). These through-holes can tie, for example, into a series of conductive track wires disposed on the interconnect layer, which track wires connect to a "spinal cord", such as a cable bundle, flat cable or ribbon cable that runs through the device.

It is also possible to use a conductive material as the substrate layer 10, particularly where the active members are to be activated simultaneously. The conductive substrate layer 110 can in turn be connected directly or indirectly to the power source or ground. Such an embodiment allows for the efficient distribution of power within the device, particularly where a highly conductive substrate material such as a metal foil is used as the substrate layer 110.

Although not illustrated in FIG. 2B, it may be desirable to provide a barrier layer between the substrate layer 110 and the outside environment, particularly where a conductive substrate layer 110 is used.

Polymeric materials preferred for use in the construction of the substrate layer 110 are biocompatible, biostable polymers (i.e., polymers that do not substantially degrade in vivo). Preferred biocompatible, biostable polymers include numerous thermoplastic and elastomeric polymeric materials that are known in the art. Polyolefins such as metallocene catalyzed polyethylenes, polypropylenes, and polybutylenes and copolymers thereof; ethylenic polymers such as polystyrene; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethylene terephthalate (PET); polyester-ethers; polysulfones; polyamides such as nylon 6 and nylon 6,6; polyamide ethers; polyethers; elastomers such as elastomeric polyurethanes and polyurethane copolymers; silicones; polycarbonates; and mixtures and block or random copolymers of any of the foregoing are non-limiting examples of biostable biocompatible polymers useful for manufacturing the medical devices of the present invention.

Among the more preferred biostable polymeric materials are polyolefins, polyolefin-polyvinylaromatic copolymers including polystyrene-polyisobutylene copolymers (more preferably copolymers of polyisobutylene with polystyrene or polymethylstyrene, even more preferably polystyrene-polyisobutylene-polystyrene triblock copolymers described, for example, in U.S. Pat. No. 5,741,331, U.S. Pat. No. 4,946,899 and U.S. Ser. No. 09/734,639, each of which is hereby incorporated by reference in its entirety) and butadiene-styrene copolymers, ethylenic copolymers including ethylene vinyl acetate copolymers (EVA) and copolymers of ethylene with acrylic acid or methacrylic acid; elastomeric polyurethanes and polyurethane copolymers; metallocene catalyzed polyethylene (mPE), mPE copolymers; ionomers; polyester-ethers; polyamide-ethers; silicones; and mixtures and copolymers thereof.

Where a conductive substrate layer 110 is desired, preferred materials include metals, such as gold, platinum, silver and titanium, and polymers, such as those discussed immediately above, which have been doped with one or more conductive fillers, for example, carbon black. Preferably, these materials are selected to be non-reactive with the chosen electrolyte.

The electrolyte within the electrolyte-containing layer 114 can be a liquid, a gel, or a solid as previously discussed. It is beneficial that the active members 112 avoid contact with the counter-electrode 118 to prevent short-circuiting. The characteristics of the electrolyte that is selected may prevent such contact from occurring, particularly in the case of a solid electrolyte. If not (for example, where a liquid or gel electrolyte is used), additional measures may be taken to keep the active members 112 separated from the counter-electrode 118. For example, a series of insulating polymer spacers with interstitial electrolyte can be placed between the active members 112 and the counter-electrode 118. Similarly the electrolyte may be provided within pores or perforations of an insulating polymer layer or within the interstices of a woven layer or mesh of insulating polymer. Beneficial insulating polymers for this purpose include insulating polymers within the polymer list that is provided above in connection the substrate layer 110. PTFE is a specific example.

The counter-electrode 118 may be any electrical conductor, including another conducting polymer, a conducting polymer gel, or a metal such as gold or silver.

Barrier layer 120 may be beneficial for several reasons. For example, a barrier layer 120 is provided in many cases to prevent species within the electrolyte-containing layer 114 from escaping the device. Of course, in the case where the counter-electrode layer 118 is impermeable (for example, where a gold foil layer is used as a counter-electrode), the barrier layer 120 will not be needed to perform this function.

The barrier layer 120 may also be beneficial in that it can electrically insulate the counter-electrode layer 118 from the surrounding environment. For example, in many embodiments, it is desirable to connect the counter-electrode 118 to the appropriate terminal of a power source. On the other hand, in the absence of an insulating barrier layer 120, the counter-electrode layer 118 will be in contact with the body, which may be desirable where the body serves as an electrical ground for the device.

Preferred materials for the barrier layer 120 include the polymeric materials discussed above in connection with the substrate layer 110.

The specific cross-section illustrated in FIG. 2B also includes a flexible mesh layer 122, which can be composed of any number of biocompatible materials, including metallic or polymeric materials. The mesh layer 122 can serve several purposes. For example, in the event the mesh layer is placed adjacent tissue in the patient, fibrotic tissue in-growth can occur, further securing the device to the tissue.

The mesh layer 122 can also act as a structural element that provides a mechanical bias to the device 100. For example, an elastic mesh layer 122 can be disposed such that it biases the artificial sphincter to its extended state.

More generally, in some embodiments, the devices of the present invention are provided with a restoring force that biases the device toward a preselected configuration. In such embodiments, the active members are used to move the device away from this preselected configuration. For example, the device can include one or more structural elements that are sufficiently elastic to restore the device to an expanded configuration upon relaxation of the active members within the device. The device can be changed into a contracted configuration by simply contracting the active members disposed within the device. The mesh layer 122 constitutes but one way in which this restoring force may be provided.

The various layers of the device of FIG. 2A are preferably registered with one another and the layers are bonded together to form a unitary mass using a number of suitable known techniques. Such techniques may include, for example, lamination, spot welding, the use of an adhesive layer or a tie layer, and so forth.

Although not illustrated, the edges of the structure of FIG. 2B are preferably sealed, for example, to avoid release of electrolyte and to avoid electrical edge effects. This can be accomplished in a number of ways. As a specific example, this objective can be achieved by extending the substrate layer 110 (if insulating) and the barrier layer 120 beyond the other components (i.e., beyond the active members 112, electrolyte containing layer 114, and counter-electrode 118). This allows the substrate layer 110 and the barrier layer 120 to be joined to one another, forming an encapsulating structure.

In general, the extent of contraction of the devices of the present invention will be determined by the voltage of the power supply in combination with the intrinsic position-dependent electrical properties of the active member. However, if desired, the devices sphincter may be provided with one or more sensors, such as piezoelectronic or conductive polymer strain gauges, to provide electronic feedback concerning the orientation of the device.

In some embodiments, a drug delivery coating (not illustrated) is provided outside the device for selective, time-dependent, long-term delivery of therapeutics. Lubricous coatings such as hydrogel coatings (not illustrated) can also be provided on at least a portion of the device surface for easier placement.

Figure 5A:
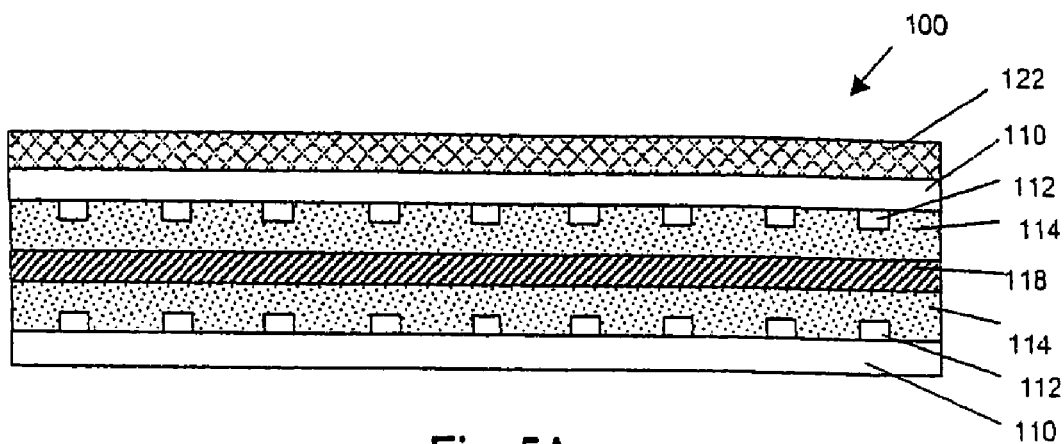
FIGS. 5A–5C are alternate schematic cross-sectional views of the artificial sphincter cuff of FIG. 2A taken along line A–A', in accordance with various embodiments of the invention.

In instances where two or more layers of active members 112 are employed, a layer stack like that illustrated in FIG. 5A can be used. By comparing this stack with that of FIG. 2B, it can be seen that the upper barrier layer 120 is replaced with an additional substrate layer 110 having attached active members 112 (one numbered). In this particular configuration, both substrate layers 110 are insulators, so the additional substrate layer 110 acts as a barrier layer. The active members 112 attached to the upper and lower substrate layers 110 are separated from a common counter-electrode 118 by electrolyte-containing layers 114.

Figure 5B:
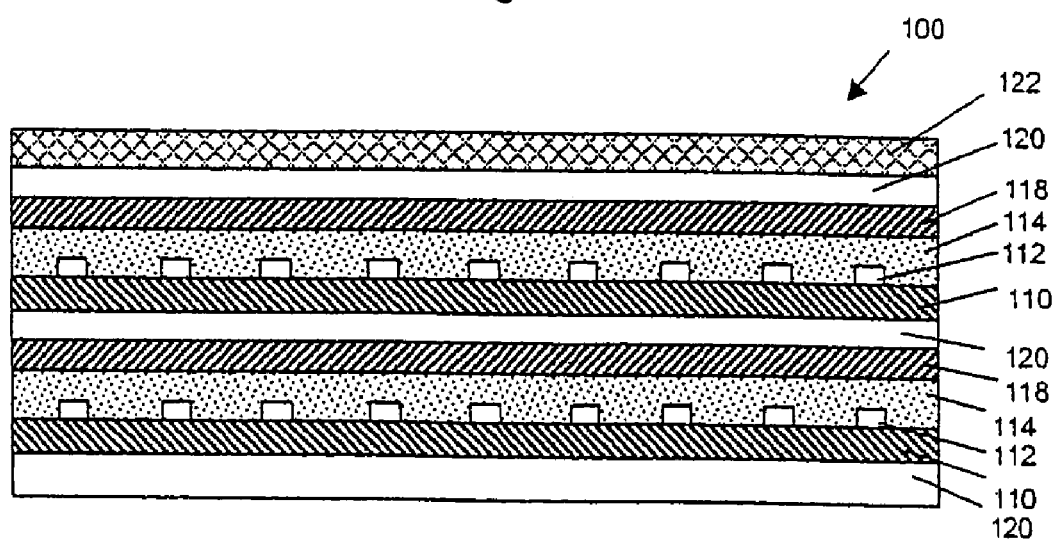

Other configurations are also possible. For example, various layers can be repeated as necessary to yield the final structure. Referring to FIG. 5B, for instance, two (or more) sets of the following layers can be implemented as desired: (a) an insulating barrier layer 120, (b) a conductive substrate layer 110 with active members 112, (c) electrolyte-containing layer 114 and (c) counter-electrode layer 118.

Figure 5C:
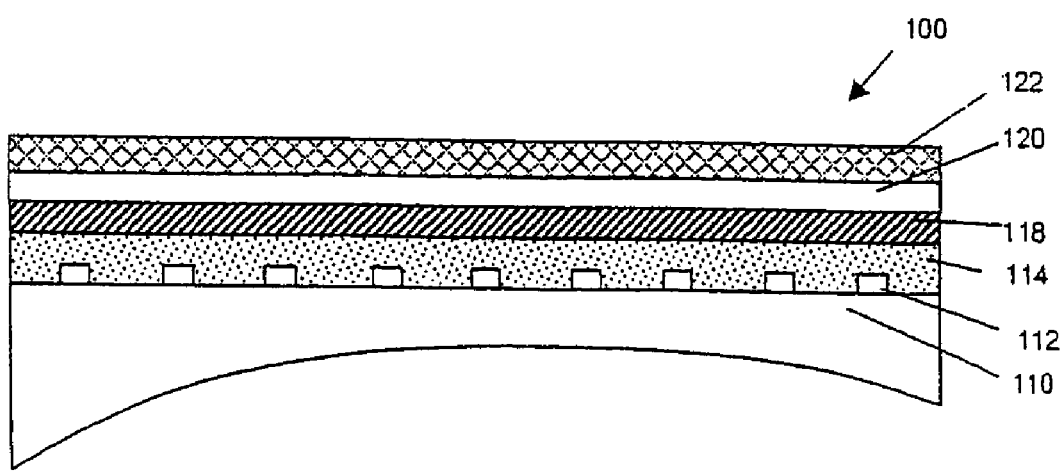

It is noted that devices of essentially constant cross-sectional thickness have been exemplified in the above embodiments. However, it is desirable in some embodiments to vary the cross-sectional thickness of the device, for example, to better reflect the anatomical contour of the tissue to which the device is attached and/or to affect the manner in which the device acts upon that tissue. An example of a device having a variable cross-section is illustrated in FIG. 5C. In FIG. 5C, the variable cross-section of the device is provided by including a substrate 110 of variable cross-section. Other layers, or combinations of layers, can be used to achieve this effect. However, the active members 112, which are generally on the order of about 30 microns in thickness, are less useful for this purpose as they typically do not exhibit substantial changes in thickness.

The devices of the present invention are adapted to be surgically inserted into the body of a patient. For example, the devices of the invention can be used as artificial urethral sphincter cuffs to remedy urinary incontinence by providing a substitute for defective urethral sphincter muscles.

Figure 6A:
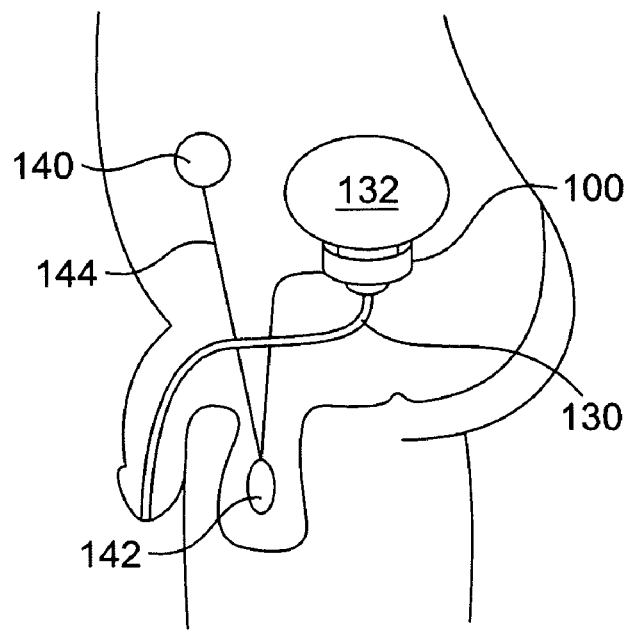
FIGS. 6A and 6B are schematic perspective views illustrating the deployment, within a man and a woman, respectively, of an artificial urethral sphincter, in accordance with embodiments of the invention.
Figure 6B:
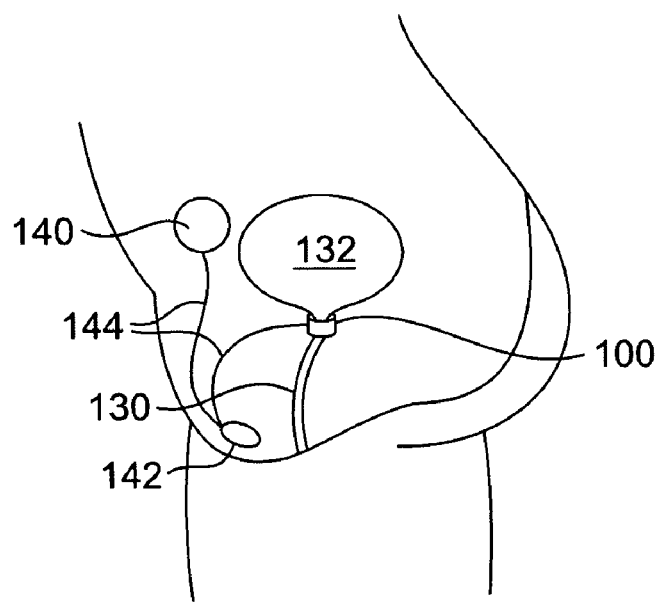

Referring now to FIGS. 6A and 6B, an artificial urethral sphincter in accordance with the present invention may be surgically implanted within a human torso. An artificial sphincter cuff 100 circumscribes urethra 130, which extends from the bladder 132 to the outside environment. In these embodiments, the voltage source 140 is located within the abdominal cavity, and a switch 142 is located within the scrotum in the case of a male patient or the labia in the case of a female patient, so that it may be externally manipulated by pressing it through the skin. Of course, switches that do not require the user to physically contact them, such as magnetically controlled or radio controlled switches, can also be used. The voltage source 140, switch 142 and artificial sphincter cuff 100 are electrically interconnected via cables 144.

The artificial sphincter can be implanted within the trunk using either an open technique or a laproscopic technique (an endoscopic technique is also possible) by first making an abdominal incision through the skin overlying the abdominal cavity. After the urethra 130 is exposed, the cuff 100 is wrapped around it and the ends secured to one another. The cuff 100 is wrapped, for example, around the bladder neck in most women and around the bulbous urethra in most males. This implantation procedure is analogous to prior art artificial sphincter implantation procedures, in which a cuff is placed around the urethra, a pressurized source is placed in the abdominal cavity, and a squeeze pump is placed in the scrotum or labia.

The voltage source 140 may be replaceable, for example by a surgical procedure, or rechargeable, for example, by magnetic coupling or by connecting external leads to the device.

Figure 7A:
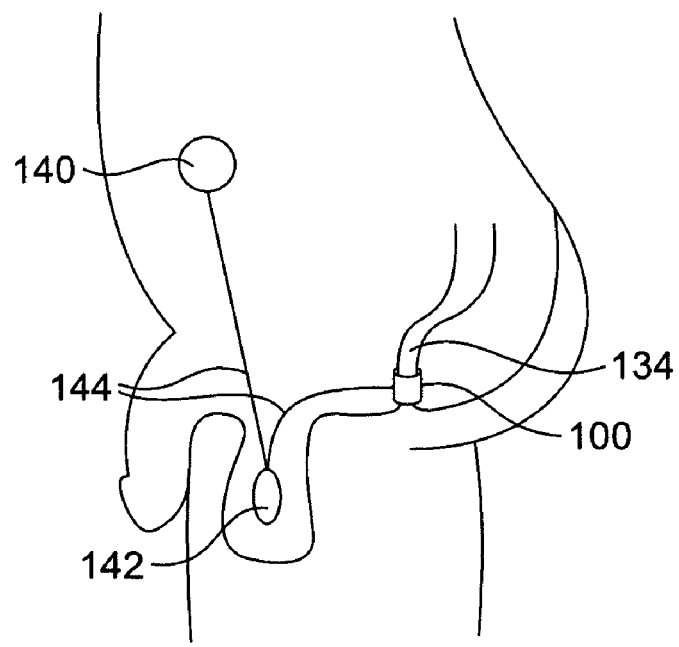
FIGS. 7A and 7B are schematic perspective views illustrating the deployment, within a man and a woman, respectively, of an artificial anal sphincter, in accordance with embodiments of the invention.
Figure 7B:
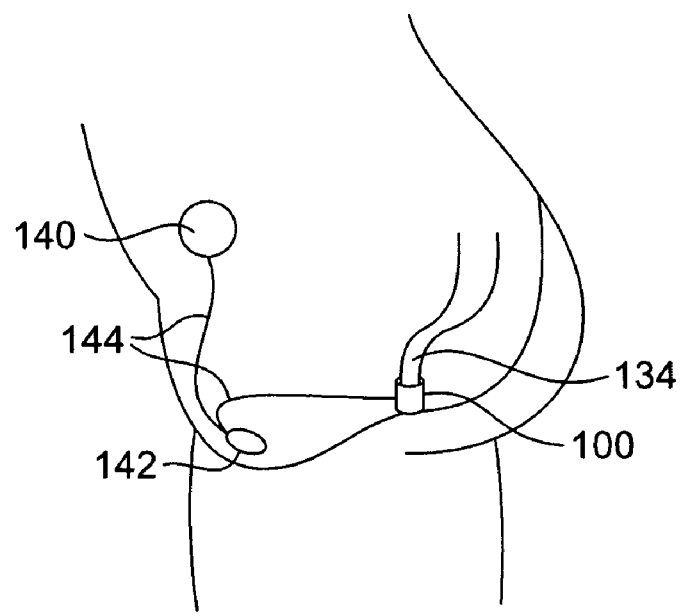

The artificial sphincters of the invention can also be used as anal sphincters to remedy fecal incontinence by providing a substitute for defective anal sphincter muscles. Referring now to FIGS. 7A and 7B, the artificial sphincters are surgically implanted within a human torso such that cuff 100 of the artificial sphincter circumscribes the anal canal 134. As with the above embodiments directed to the implantation of an artificial urethral sphincter, a voltage source 140 is typically located within the abdominal cavity, and a switch 142 is preferably located within the scrotum in the case of a male patient or the labia in the case of a female patient.

The artificial sphincter can be implanted within the trunk, for example, by making a first incision around the anus to allow the cuff member 100 to be implanted around the anal canal 134 and by making a second incision into the lower abdominal area to implant the voltage source 140 and switch 142. This implantation procedure is analogous to prior art artificial anal sphincter implantation procedures, in which a cuff is placed around the anal canal, a pressurized balloon is placed in the abdominal cavity and a squeeze pump is placed in the scrotum or labia. Such procedures are presently used, for example, in the implantation of the Acticon™ Neosphincter, a product of American Medical Systems, Inc., which the U.S. Food and Drug Administration (FDA) has granted approval to market in the United States for the treatment of severe fecal incontinence.

Figure 8A:
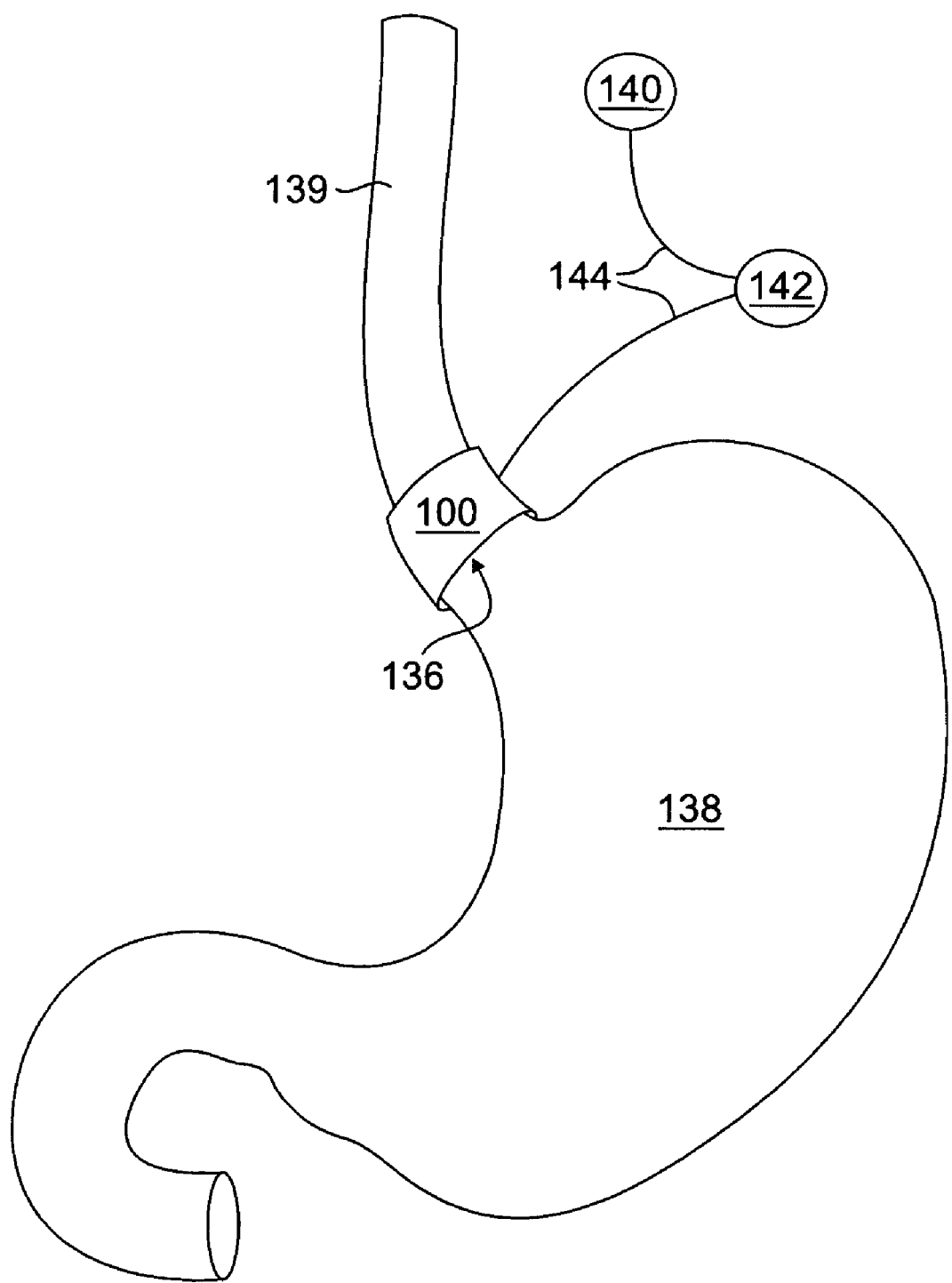
FIGS. 8A–8C are schematic perspective views illustrating the deployment of artificial lower esophageal sphincters within a patient, in accordance with various embodiments of the invention.

Artificial sphincters in accordance with the present invention can also be used to reinforce the operation of the lower esophageal sphincter, for example, in patients experiencing chronic GERD. Referring now to FIG. 8A, an artificial sphincter is surgically implanted within a human torso, such that a cuff 100 of the artificial sphincter circumscribes the existing lower esophageal sphincter 136, which is found at the end of the esophagus 139 adjacent the stomach 138. A voltage source 140 and a switch 142 (or other control unit) are typically located under the fascia in the vicinity of the peritoneum. In the embodiment illustrated, the voltage source 140, switch 142 and artificial sphincter cuff 100 are electrically connected via cables 144. The artificial sphincter can be implanted within the trunk by procedures akin to those used in performing known fundoplication processes, including both open and laproscopic procedures.

Although the cuff portion 100 of the artificial sphincter of FIG. 8A (as well as those of FIGS. 6A, 6B, 7A and 7B above) is preferably of a design akin to that discussed above in connection with FIGS. 2A and 2B, other designs are possible. For example, referring now to FIG. 8B, an artificial lower esophageal sphincter is illustrated that, like the artificial lower esophageal sphincter of FIG. 8A, includes a cuff portion 100, which is operated by voltage source 140 and switch 142. Leads 143 and cables 144 are provided to connect respective terminals of the voltage source 140 with the counter-electrode and the active members found within the sphincter cuff 100.

Figure 8B:
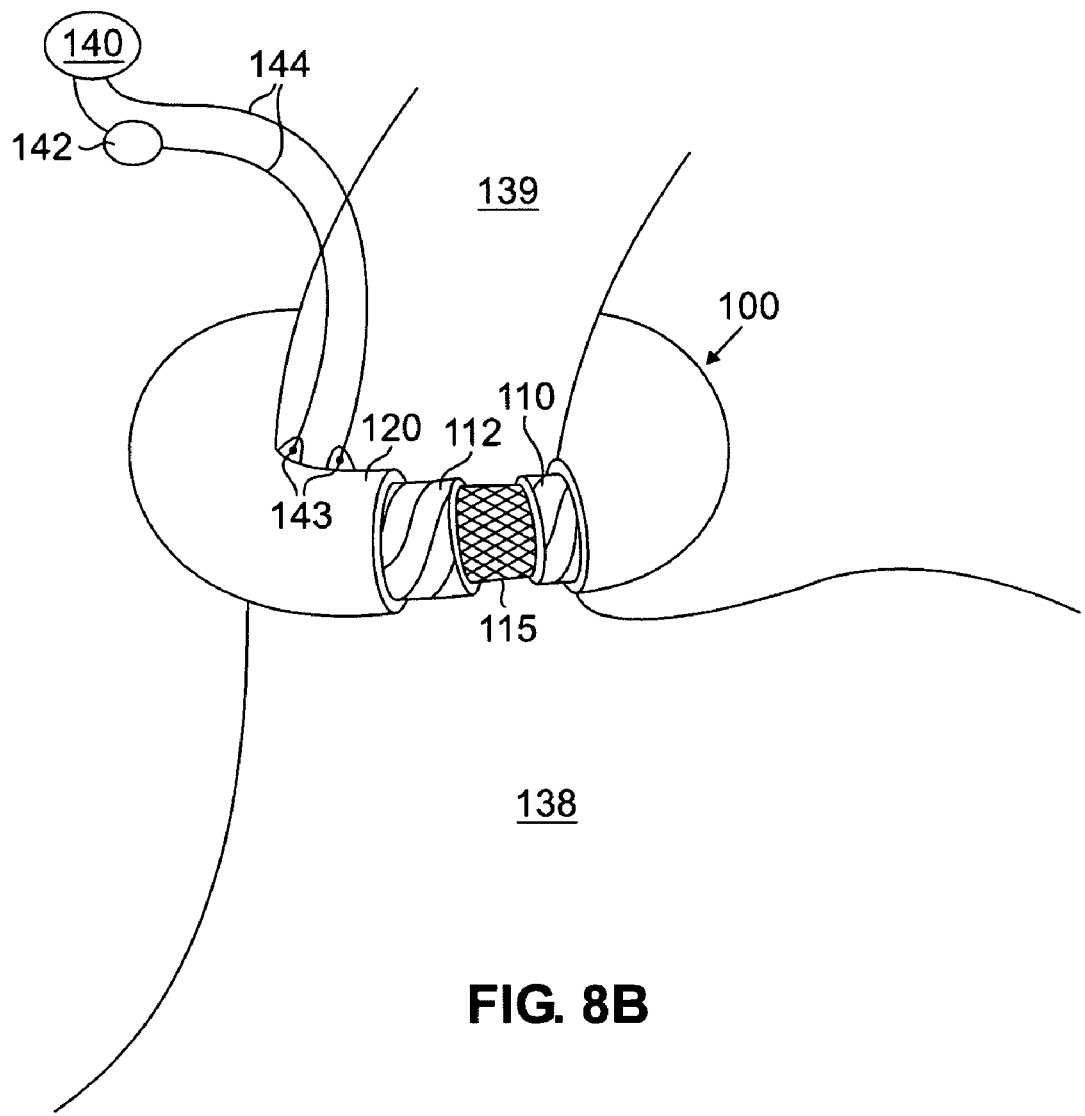

At the core of the cuff 100 illustrated in FIG. 8B is an annular wire mesh tube 115. The wire mesh tube 115 (wire mesh structures of this type are well known, for example, in the art relating to vascular and other endoluminal stents) is preferably constructed of an elastic plastic or metal material, such as nitinol, elgiloy and/or other shape memory metal or polymer. Surrounding the wire mesh tube 115 is a group of active members 112 (one numbered), which are preferably disposed on a substrate layer 110 as discussed above in connection with FIG. 2B. Although not illustrated, an electrolyte-containing layer is typically disposed between the active members 112 and a counter-electrode. Finally, a barrier layer 120 is provided over the entire assembly.

When the active members 112 are contracted, the diameter of the tubular cross-section of the wire mesh tube 115 is reduced, increasing the overall length of the tube (much like the children's toy known as the "Chinese finger trap" lengthens as it tightens its grasp on one's fingers). As a result, the cuff portion 100 is loosened, opening the lumen that it surrounds (i.e., the lower esophagus). Conversely, when the active members are relaxed, the tubular cross-section of the wire mesh tube 115 increases (due to its inherent elasticity), shortening the overall length of the tube 115 and thereby constricting the lumen.

Structures other than the above wire mesh tube 115 can also be used, including compliant tubular ring structures with variable stent-like cell geometry or with a plurality of individual modules configured radially or spirally, to enable opening and closing functions that are analogous to a camera aperture. Double annular structures can also be used, for example, where the inside annulus is provided with the electroactive polymer actuators and the outer annulus is static.

In simpler embodiments, such at those discussed immediately above, the artificial lower esophageal sphincter employs a switch that is operated by a patient, for example, when the patient wishes to swallow, belch or vomit. The switch can be placed at a position such as under the skin at the chest or side, where it can be physically operated by the patient or where it can be operated by, for example, magnetic or radio control.

In more complex, automated embodiments of the invention one or more sensors provide a computer, or other suitable control unit, with information that the computer uses to make a decision as to whether or not to open the lower esophageal sphincter.

For instance, as noted above, the lower esophageal sphincter normally opens in response to the peristaltic motion that is triggered when food or beverage enters the esophagus. After food passes into the stomach, the peristaltic motion ceases, and the lower esophageal sphincter returns to its normal resting state to prevent reflux of the stomach contents, including stomach acid, back into the esophagus. In some embodiments of the invention, one or more sensors are provided that are capable of sensing the peristaltic state of the esophagus. For example, peristaltic motion can be detected by one or more strain gauges. For example, piezoelectric sensors can function as strain gauges. Alternatively, electroactive polymers can be used as a signal generating materials for this purpose. Alternatively, the electrical changes associated with the peristaltic motion of the esophagus can be measured by inserting one or more electrical sensors into the esophagus. Similar piezoelectric and electrical sensor technologies have been developed, for example, in connection with heart rate monitoring systems.

The lower esophageal sphincter should also open in response to the need to belch or regurgitate. As with swallowing, one or more sensors (e.g., piezoelectric sensors) may be provided that are capable of sensing the deformation of the stomach that is associated with the need to perform one of these functions. Alternatively, electrical sensors can be used to detect the associated electrical signals. In the case of regurgitation, pH sensors can also be used, as regurgitation is typically associated with a substantial change in pH.

In each case, a computer or other logic device preferably analyzes the signals from the sensors using an appropriate algorithm. Once it is determined by the computer that appropriate conditions are present, a control signal is sent to the artificial lower esophageal sphincter to open it.

Even with the use of sensors, however, it may be preferred to have a manual backup switch that is accessible to the user in the event of system failure. A backup power source, for example one outside the body, may also be desired in the event that the internal power source 140 fails. The backup power source can be connected using the same electrical circuitry that is discussed above in connection with recharging the internal power source 140.

Figure 8C:
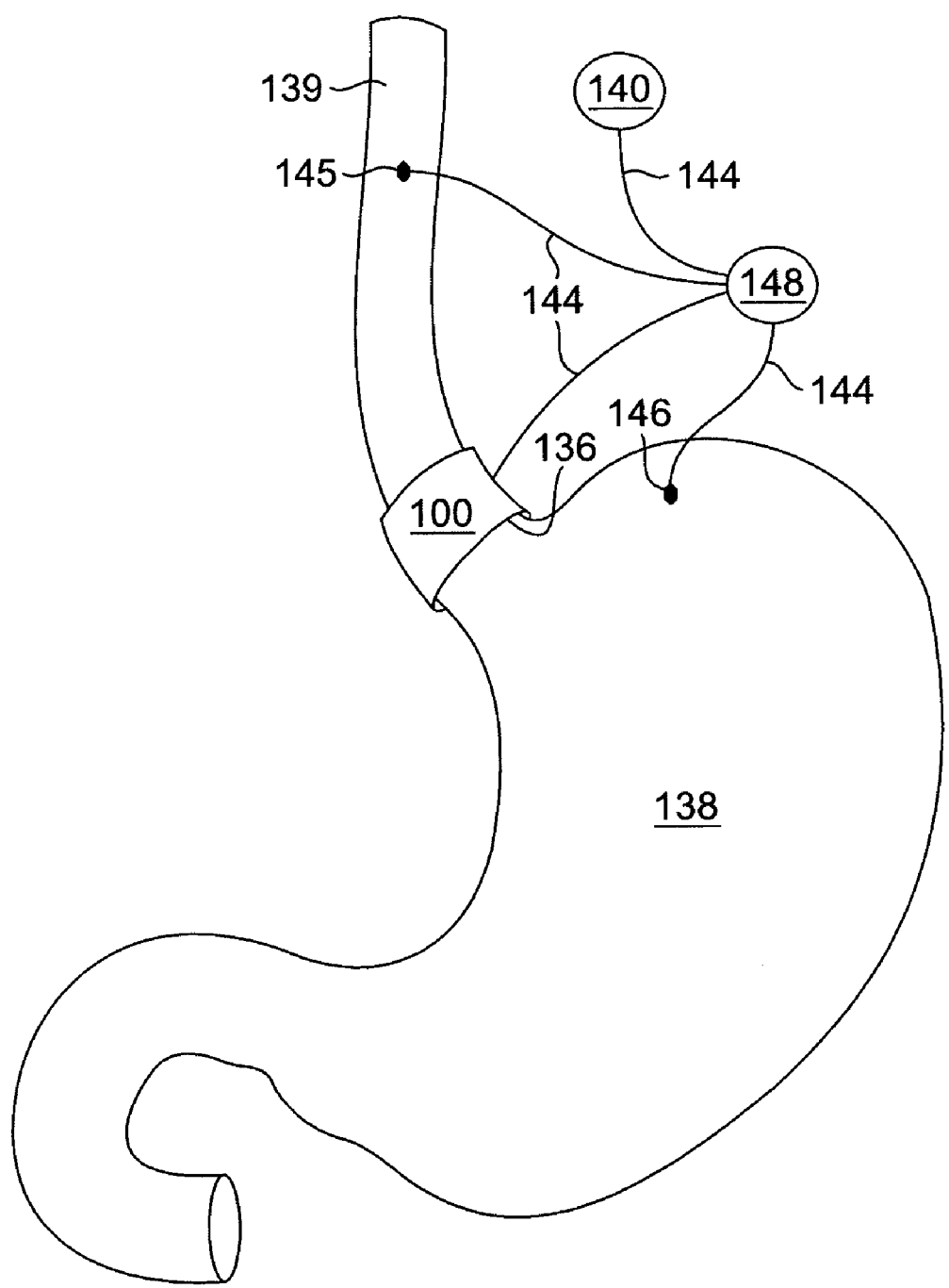

Referring now to FIG. 8C, a lower esophageal sphincter system is illustrated that includes the artificial sphincter cuff 100 and the voltage source 140 illustrated in FIG. 8A. In addition, sensors 145, 146 are provided on the esophagus and on the stomach, respectively, which provide input to a signal analysis and control unit 148, preferably a computer. Components that may be provided within the signal analysis and control unit 148 include signal converters (e.g., analog-to-digital and digital-to-analog converters), signal amplifiers, and or more microprocessors.

As an example, the signals from the sensors 145, 146 can be amplified and converted into digital signals, as required. Subsequently, the signals from the sensors 145, 146 are analyzed by the microprocessor using a suitable algorithm. Upon receipt of an appropriate signal(s) from the sensors 145, 146, an output signal is sent to the cuff portion 100 of the artificial sphincter, using any required signal converters and/or amplifiers, relaxing the cuff portion 100.

Figure 9A:
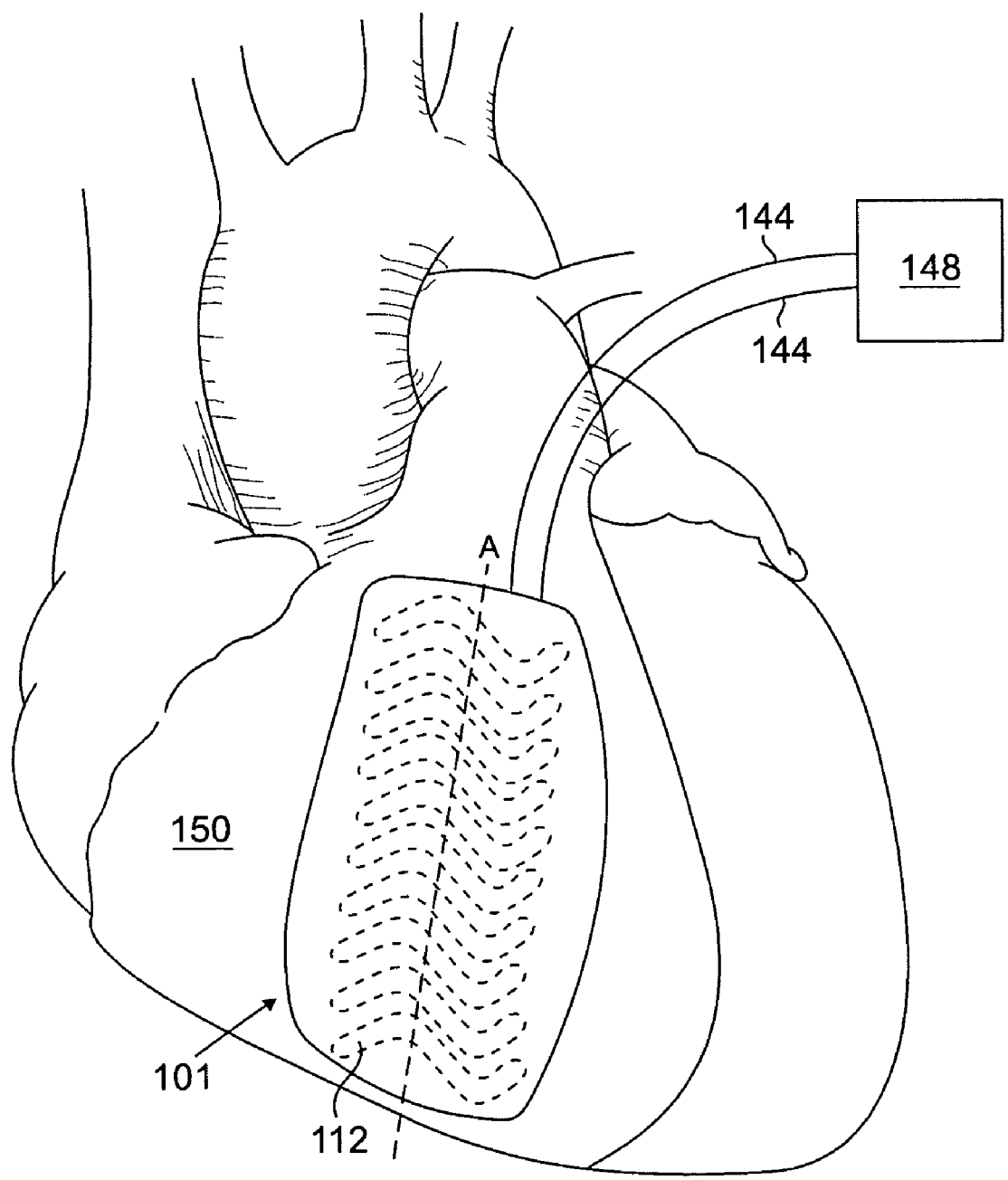
FIG. 9A is a schematic perspective view illustrating the deployment upon the heart of an artificial muscle patch, in accordance with an embodiment of the invention.

Other embodiments of the invention relate to artificial muscles patches, which can, among other things, make up for loss of muscle function within compromised tissue. Referring now to FIG. 9A, a heart 150 is illustrated having affixed thereto an artificial muscle patch 101. The patch 101 illustrated occupies an area generally corresponding to the left ventricle of the heart.

The internal active members 112 (one numbered) are illustrated with hidden lines in FIG. 9A. As with the above artificial sphincter devices, the active members 112 within the artificial muscle patch of FIG. 9A can be disposed within the patch in a number of ways, including the disposition of arrays of active members upon one or more sheets of substrate material within the device.

Figure 9B:
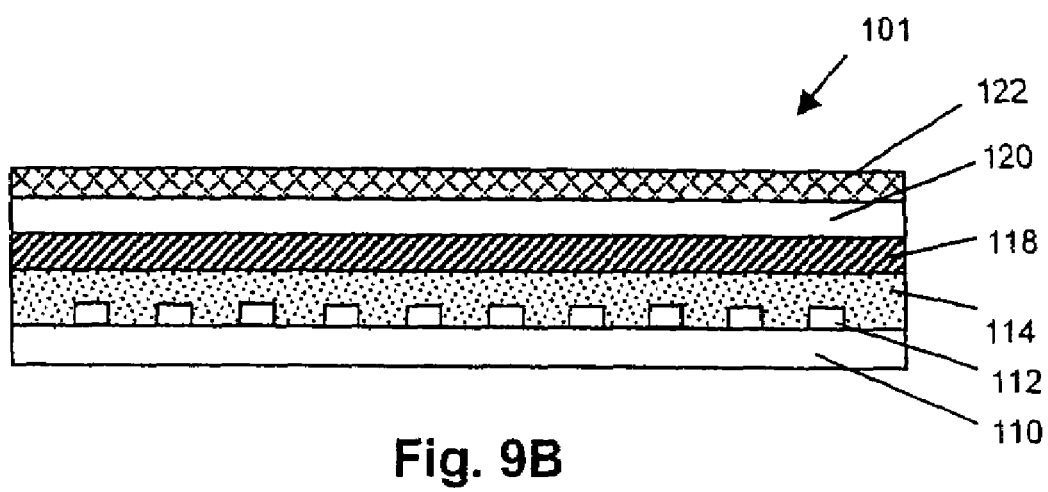
FIG. 9B is a schematic cross-sectional view of the artificial muscle patch of FIG. 9A, taken along line A–A'.

In this connection, a cross-sectional view taken along line A–A' of FIG. 9A is illustrated in FIG. 9B. The cross-sectional view of FIG. 9B is essentially the same as that illustrated in FIG. 2B. FIG. 9B illustrates a substrate layer 110 upon which several active members 112 (one numbered) are disposed. An electrolyte-containing layer 114 is disposed over the active member(s) 112, and a counter-electrode 118 is disposed in turn over the electrolyte-containing layer 114. Barrier layer 120 and mesh layer 122 are provided over counter-electrode 118. These layers are discussed in more detail above. In general, the mesh layer 122 is placed adjacent heart tissue in the patient, allowing fibrotic tissue in-growth to occur, further securing the device to the heart tissue.

Although not illustrated, patch 101 can be provided with a series of suture holes along its circumference that allow the patch to be sutured to the heart. The sutures can be tightened during diastole, for example, for a tight fit.

Although the patch 101 in FIG. 9A occupies an area outside the left ventricle of the heart, patches in accordance with the present invention can be placed over other areas as needed, including the area outside the right ventricle, or any area where the physical properties or the muscle cell activity of the heart has been compromised.

Furthermore, in some embodiments, the patch may be configured such that it completely wraps around the lower portion of the heart. The opposing ends of the patch can then be secured to one another using fastening techniques such as those discussed above in connection with various artificial sphincter designs. As with suturing, fasteners can be fitted snug during diastole.

Because the active members can be deposited on a film of variable thickness, a near-infinite range of 3-dimensional active member configurations can be achieved. For example, the active members can be configured in three-dimensional space to push inward on the heart tissue in a fashion akin to that observed with natural heart muscle strands.

The artificial muscles patch 101 of FIG. 9A is placed in electrical communication with a control unit 148 (which typically contains a power supply and some form of control, such as a switch or a computer) via control cables 144.

As previously noted, the active members 112 within the devices of the present invention can be either controlled as a group or individually controlled. Where controlled as a group, the active members 112 can simply be placed in a mode where they are in a constantly contracted state, allowing the patch to act as a simple cardiac constraint device in this instance. A simple switch is all that is required for electrical control of the active members in this case.

The active members 112 can also be controlled as a group in a pulsed fashion to approximate the function of heart muscles. In this instance, the control unit will typically include a pacing unit, which can be used to both pace the heart muscles and the active members of the artificial muscle patch. Pacing of the artificial muscle patch 101 can, for example, assist heart contraction during systole.

Alternatively, a sensor (not shown) can be used to determine the natural pace of the heart. The signal from this sensor (after amplification and digitization, if required) can be fed into a computer or other logic device where it is analyzed (using, for example, an appropriate algorithm) to determine pacing of the signal that is sent to the active members 112 within the artificial muscle patch.

In other embodiments, the active members 112 are all paced in accordance with the overall heart rate, but are also actuated at slightly different times in accordance with a suitable algorithm. In this case, as previously discussed, individual cables can be provided to individually activate the active members 112 or an appropriate multiplexing scheme can be used.

As above, the extent of contraction of the active members will typically be determined by the voltage of the power supply in combination with the intrinsic, position-dependent electrical properties of the active member. However, if desired, the artificial muscle patch may be provided with a plurality of sensors, such as strain gauges, to provide electronic feedback concerning the orientation of the device.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed:

1. An artificial sphincter, comprising:
   a cuff that is adapted for placement around a body lumen, said cuff comprising an electroactive polymer actuator comprising a conductive polymer active member that is disposed on a substrate layer in a non-linear configuration; and
   a control unit electrically controlling said one or more electroactive polymer actuators to expand or contract said cuff.

2. The artificial sphincter of claim 1, wherein said electroactive polymer actuator comprises (a) said active member, (b) a counter-electrode and (c) an electrolyte disposed between said active member and said counter-electrode.

3. The artificial sphincter of claim 1, wherein a pluraty of said active members are disposed on said substrate layer.

4. The artificial sphincter of claim 3, further comprising at least one barrier layer.

5. The artificial sphincter of claim 4, further comprising an exterior mesh layer.

6. The artificial sphincter of claim 1, wherein said non-linear configuration is an s-shape configuration.

7. The artificial sphincter of claim 3, wherein at least two of said substrate layers are provided.

8. The artificial sphincter of claim 1, wherein said substrate layer is an insulating layer.

9. The artificial sphincter of claim 8, wherein conductive lines are provided on said substrate layer to allow electrical communication between said one or more active members and said power source.

10. The artificial sphincter of claim 1, wherein said substrate layer is a conductive layer.

11. The artificial sphincter of claim 1, wherein opposing ends of said cuff are provided with fasteners for securing said cuff around said body lumen.

12. The artificial sphincter of claim 1, wherein said control unit comprises a power source and a switch.

13. The artificial sphincter of claim 1, wherein said cuff is adapted for placement around the urethra.

14. The artificial sphincter of claim 1, wherein said cuff is adapted for placement around the anal canal.

15. The artificial sphincter of claim 1, wherein said cuff is adapted for placement around the lower esophagus.

16. The artificial sphincter of claim 15, further comprising a sensing system in communication with said control unit for detecting when food or beverage enters said esophagus.

17. The artificial sphincter of claim 15, further comprising a sensing system in communication with said control unit for detecting when the stomach is attempting to regurgitate its contents.

18. The artificial sphincter of claim 1, wherein said electroactive polymer actuator comprises an electroactive polymer selected from the group consisting of polyaniline, polypyrrole, and polyacetylene.

19. The artificial sphincter of claim 18, wherein said electroactive polymer is polypyrrole.

20. The artificial sphincter of claim 1, wherein said cuff is provided with a restoring force to bring it into an expanded or contracted state.

21. The artificial sphincter of claim 20, further comprising at least one elastic structural element, wherein said restoring force is provided by the structural element.

22. The artificial sphincter of claim 21, wherein said at least one elastic structural element is an elastic annular tube structure whose length increases upon a decrease in its cross-sectional diameter.

23. The artificial sphincter of claim 1, further comprising a sensing system in communication with said control unit for sensing the degree of contraction of said electroactive polymer actuator.

24. The artificial sphincter of claim 23, wherein said sensing system in communication with said control unit comprises a plurality of strain gauges.

25. A method of treating fecal incontinence comprising implanting into a patient the artificial sphincter of claim 14.

26. A method of treating urinary incontinence comprising implanting into a patient the artificial sphincter of claim 13.

27. A method of treating gastro-esophageal reflux disease comprising implanting into a patient the artificial sphincter of claim 15.

28. The artificial sphincter of claim 1, wherein said control unit comprises a power source and a computer.

29. An artificial muscle patch, comprising:
   an actuator comprising a conductive polymer active member that is disposed on a substrate layer in a non-linear configuration; and
   a control unit electrically controlling said electroactive polymer actuator to expand or contract said artificial muscle patch, wherein said patch is adapted to be implanted adjacent a patient's heart.

30. The artificial muscle patch of claim 29, wherein said electroactive polymer actuator comprises (a) said active member, (b) a counter-electrode and (c) an electrolyte disposed between said active member and said counter-electrode.

31. The artificial muscle patch of claim 29, wherein a plurality of said active members are disposed on said substrate layer.

32. The artificial muscle patch of claim 31, which further comprises at least one barrier layer.

33. The artificial muscle patch of claim 32, further comprising an exterior mesh layer.

34. The artificial muscle patch of claim 29, wherein said nonlinear configuration is an s-shaped configuration.

35. The artificial muscle patch of claim 31, wherein at least two of said substrate layers are provided.

36. The artificial muscle patch of claim 29, wherein said substrate layer is an insulating layer.

37. The artificial muscle patch of claim 36, wherein conductive lines are provided on said substrate layer to allow electrical communication between said one or more active members and said power source.

38. The artificial muscle patch of claim 29, wherein said substrate layer is a conductive layer.

39. The artificial muscle patch of claim 29, wherein said control unit comprises a power source and a switch.

40. The artificial muscle patch of claim 29, wherein said control unit comprises a power source and a computer.

41. The artificial muscle patch of claim 29, further comprising a sensing system in communication with said control unit for detecting a patient's heartbeat, wherein said control unit paces the contraction and expansion of said electroactive polymer actuators with said heartbeat.

42. The artificial muscle patch of claim 29, wherein said control unit paces the heart as well as the contraction and expansion of said electroactive polymer actuators.

43. The artificial muscle patch of claim 29, wherein said electroactive polymer comprises polypyrrole.

44. A method of treating congestive heart failure, comprising implanting the artificial muscle patch of claim 29 adjacent a patient's heart.

* * * * *